US006129659A

United States Patent [19]

Wilk

[11] Patent Number: 6,129,659

[45] Date of Patent: Oct. 10, 2000

[54] COLD THERAPY PAD WITH MAGNETOTHERAPY INSERT

[76] Inventor: Bruce R. Wilk, 9880 SW. 110th St., Miami, Fla. 33176

[21] Appl. No.: 09/261,290

[22] Filed: Mar. 2, 1999

[51] Int. Cl.[7] .............................. A61B 17/52; A61N 2/00

[52] U.S. Cl. ................................ 600/9; 600/15; 607/108; 607/112; 607/114

[58] Field of Search ............................ 600/9, 15; 607/96, 607/104, 108–112, 114

[56] References Cited

U.S. PATENT DOCUMENTS

| | | | |
|---|---|---|---|
| 1,394,810 | 10/1921 | Craddick . | |
| 2,339,409 | 1/1944 | Joy et al. | 128/402 |
| 3,943,912 | 3/1976 | Nakayama | 128/1.3 |
| 4,850,340 | 7/1989 | Onishi | 128/24.1 |
| 4,865,012 | 9/1989 | Kelley | 126/204 |
| 5,720,046 | 2/1998 | Lopez | 2/159 |
| 5,735,889 | 4/1998 | Burkett et al. | 607/96 |
| 5,738,624 | 4/1998 | Zablotsky et al. | 600/15 X |
| 5,783,624 | 7/1998 | Khanarian et al. | 524/494 |
| 5,813,971 | 9/1998 | Broderick | 600/15 |
| 5,840,080 | 11/1998 | Der Ovanesian | 607/114 |
| 5,879,378 | 3/1999 | Usui | 607/108 X |

OTHER PUBLICATIONS

Advertisement for BMI Therapy, with article "How do NFL stars fight pain without chemicals or surgery?", by C. Eddie Vernon.

*Primary Examiner*—Cary O'Connor
*Assistant Examiner*—Ryan Carter
*Attorney, Agent, or Firm*—David P. Gordon; David S. Jacobson; Thomas A. Gallagher

[57] ABSTRACT

A cold therapy pad includes a flexible envelope containing a high thermal capacity gel which will remain cold for a period of time after being frozen and a flexible permanent magnet contained within the envelope. According to a presently preferred embodiment, the envelope is made of a flexible polymer such as vinyl, the thermal gel is made of silicate, and the permanent magnet is made of molten metal hardened in an electric field. The magnet may be embedded in the gel so that it is substantially centrally located relative to the envelope. If desired, the magnet may be located between the envelope and the gel. The basic construction of the invention lends itself to many geometric configurations and sizes. In different embodiments, the therapy pad is dimensioned to overlie particular body parts such as joints, limbs, the neck, the waist, the chest, and the eyes. In some embodiments VELCRO® strips are provided to affix the therapy pad to a body part. In other embodiments multiple magnets are arranged in the envelope to overlie accupressure points when the envelope is attached to the body of a user.

20 Claims, 3 Drawing Sheets

16

14

12

10

COLD THERAPY PAD WITH MAGNETOTHERAPY INSERT

BACKGROUND OF THE INVENTION

1. Field of the Invention

The invention relates to therapy pads which are applied to parts of the human body in order to ease pain and facilitate healing. More particularly, the invention relates to a cold therapy pad with a magnetic insert for simultaneously applying cold therapy and magnetic therapy.

2. State of the Art

Magnetic therapy (or magnetotherapy) is well known and widely used in the treatment of various ailments. Its effects are believed to be related to the effects of accupressure or shiatsu.

Many products are available for practising magnetotherapy and many of these are disclosed in U.S. Patents. Typical of these products are disclosed in U.S. Pat. Nos. 1,394,810; 3,943,912; 5,720,046; and 5,813,971, the complete disclosures of which are hereby incorporated by reference herein. In general, these products are wearable items which contain pockets holding permanent magnets so that magnetic fields may be applied to parts of the body.

The way in which magnetotherapy works is not fully known. Some believe that the magnetic fields act upon hemoglobin in the blood and enhance the ability of the blood to carry oxygen and nutrients to various parts of the body. See, e.g., U.S. Pat. No. 5,813,971. This mechanism would explain why magnetotherapy has effects similar to accupressure and shiatsu which tend to improve the circulation. It is perhaps with this perceived mechanism in mind that the prior art suggests that the effects of magnetotherapy may be enhanced by the application of heat in the area of the magnetic field. See, e.g. U.S. Pat. No. 1,394,810. It might be hypothesized that the heat causes the blood vessels to dilate, come closer to the surface, and thereby be more readily affected by the magnetic field.

The inventor of the present invention has discovered that, despite teachings of the art which indicate that magnetotherapy is enhanced by heat, the ailments typically treated with magnetotherapy actually respond much better to cold magnetotherapy than to warm magnetotherapy. It is the present inventor's hypothesis that the application of cold magnetotherapy is far superior to warm or temperature neutral magnetotherapy in most cases.

SUMMARY OF THE INVENTION

It is therefore an object of the invention to provide an apparatus which is adapted for the application of cold magnetotherapy.

It is also an object of the invention to provide a cold therapy pad with a magnetic insert for the application of cold magnetotherapy.

It is another object of the invention to provide a cold therapy pad with a magnetic insert which is easy to manufacture.

It is still another object of the invention to provide a cold therapy pad with a magnetic insert which may be manufactured in a variety of shapes and sizes for application to different parts of the body.

It is yet another object of the invention to provide a cold therapy pad with magnetic inserts which are located to correspond approximately to accupressure points on the human body.

In accord with these objects which will be discussed in detail below, the cold therapy pad of the present invention includes a flexible envelope containing a high thermal capacity gel which remains flexible when frozen and a flexible permanent magnet contained within the envelope. According to a presently preferred embodiment, the envelope is made of a flexible polymer such as vinyl. The presently preferred thermal gel is one which changes from liquid to slush at about 0° C. and requires considerable heat energy as it warms through this change of state from slush back to gel. Thermal gels with these qualities are described in U.S. Pat. No. 4,321,111, the complete disclosure of which is hereby incorporated by reference herein. The presently preferred gel is a silicate gel. The flexible permanent magnet is preferably about one millimeter thick and has a magnetic flux density of about 300–1,000 gauss. The magnet may be embedded in the gel so that it is substantially centrally located relative to the envelope. If desired, the magnet may be located between the envelope and the gel. The magnet may also be surrounded by inert material. The basic construction of the invention lends itself to many geometric configurations and sizes. For example, the construction of the invention may be used to make any of the wearable articles shown in the prior art patents cited above. Further, rather than using a single sleet of flexible magnet, multiple strips of flexible magnet maw be disposed within the envelope and the magnet(s) may be shaped and/or disposed in a location such that the magnet approximately overlies accupressure points in the human body when the cold therapy pad is affixed to a part of the body. The presently preferred manner of fixing the pad to the body is by providing VELCRO® strips on ends of the pad. Alternatively, elastic bands or flexible ties may be used.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
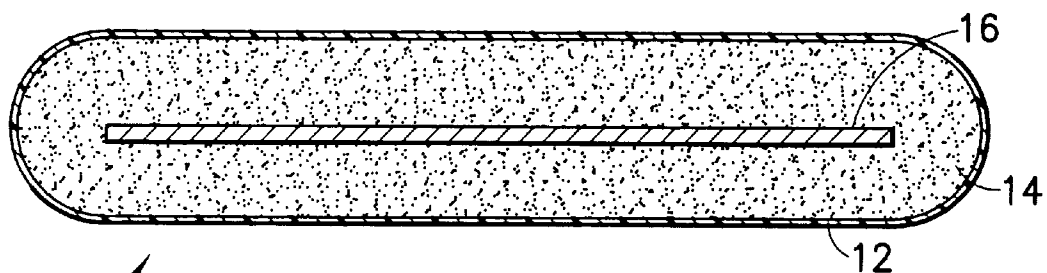
FIG. 1 is a schematic section of the basic construction of a cold therapy pad according to a first embodiment of the invention.
Figure 2:
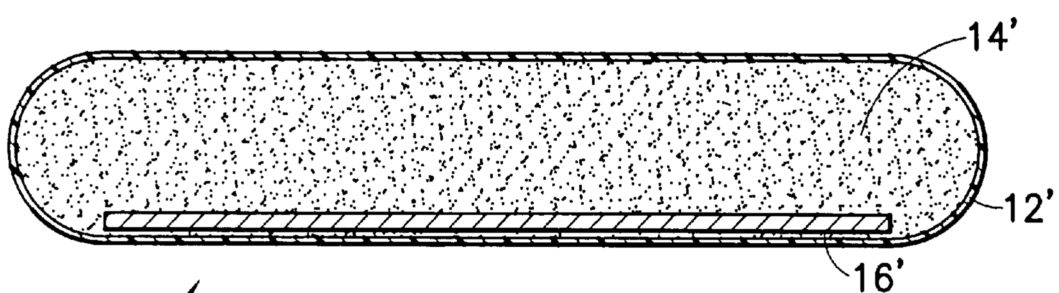
FIG. 2 is a schematic section of the basic construction of a cold therapy pad according to an alternate embodiment of the invention.

Referring now to FIGS. 1 and 2, the cold therapy pad 10 of the present invention includes a flexible envelope 12 containing a high thermal capacity gel 14 and a flexible permanent magnet 16 contained within the envelope 12. According to a presently preferred embodiment, the envelope 12 is made of a flexible polymer such as vinyl, the thermal gel 14 is a silicate, and the permanent magnet 16 is made of molter metal hardened in an electrical field. The magnet 16 may be embedded in the gel 14 as shown in FIG. 1 so that it is substantially centrally located relative to the envelope 12. If desired, the magnet 16 may be located between the envelope 12 and the gel 14 as shown in FIG. 2. The basic construction of the invention lends itself to many geometric configurations and sizes. For example, the construction of the invention may be used to make any of the wearable articles shown in the prior art patents cited above.

Figure 3:
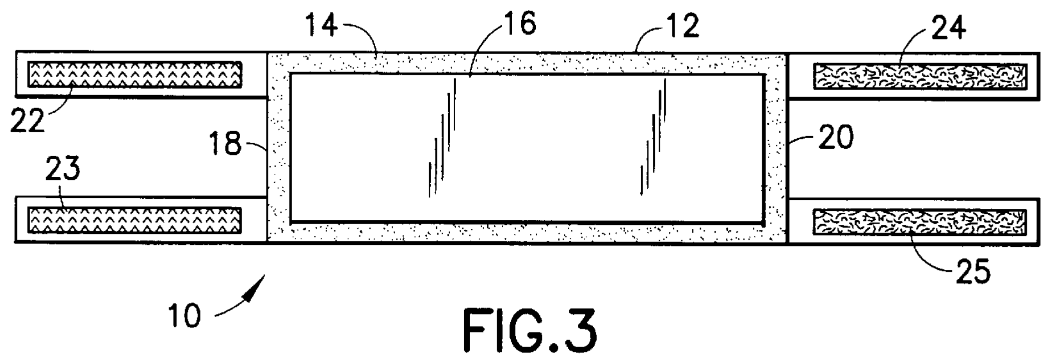
FIG. 3 is a transparent plan view of a cold therapy pad according to the invention showing VELCRO® fasteners.

Turning now to FIG. 3, a presently preferred embodiment of the cold therapy pad 10 is made from a tube or sleeve of flexible polymer 12. The gel 14 and the magnet 16 are inserted into the sleeve 12 and the sleeve 12 is welded closed at lines 18, 20. This forms a substantially flat pad having two sides and two ends. Mating VELCRO® strips are attached to the pad 10 at opposite ends on opposite sides. The structure of the pad 10 shown in FIG. 3 is ideal for attachment to a human limb by wrapping the pad around the limb and mating the VELCRO® strips 22, 24 and 23, 25. Those skilled in the art will appreciate that the dimensions of the pad 10 may be chosen such that the pad fits around an arm, a leg, a wrist, etc. Further, it will be appreciated that the dimensions of the VELCRO® strips 22, 24, 23, 25 may be chosen such that the pad 10 is adjustable to fit a variety of different sized limbs. It will also be appreciated that the dimensions of the pad 10 may be chosen such that is fits around a human waist or around a human neck.

Figure 4:
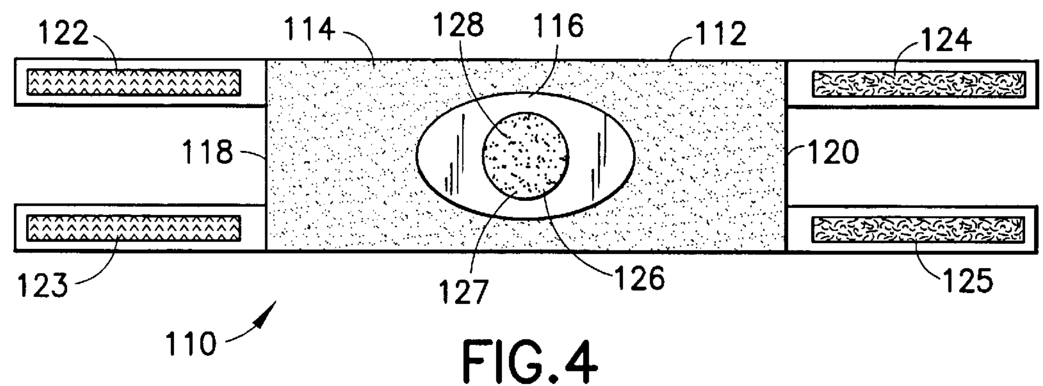
FIG. 4 is a transparent plan view of a cold therapy pad according to the invention which is designed to cover a joint such as a knee or elbow.

Referring now to FIG. 4, another embodiment of a cold therapy pad 110 is specifically designed for placement at a human joint such as the elbow or knee. The therapy pad 110 is similar to the pad 10 shown in FIG. 3 with similar reference numerals referring to similar parts. According to this embodiment, the magnet 116 is elliptical and has a central hole 126. The envelope 112 is provides with a similar hole 127 which as a diameter somewhat smaller than the hole 126. After the magnet 116 is located inside the envelope 112 with the hole 126 substantially coaxial with the hole 127, a circular weld 128 is made to seal the edges of the envelope 112 around the hole 127. The hole 127 is dimensioned to accommodate the patella or the juncture of the ulna and the humerus. When the pad 110 is attached to a knee or elbow, the elliptical magnet 116 is approximately located at the accupressure points surrounding these joints.

Figure 5:
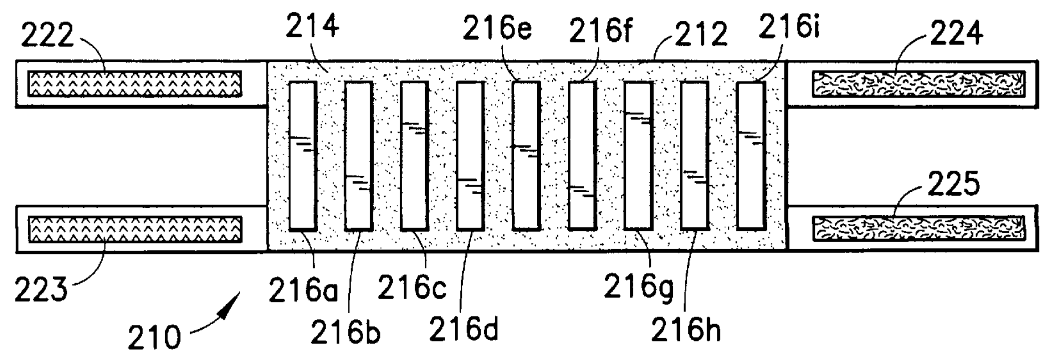
FIG. 5 is a transparent plan view of a cold therapy pad according to the invention illustrating a plurality of spaced apart magnetic strips.

Referring now to FIG. 5, another embodiment of a cold therapy pad 210 is specifically designed to place magnets approximately along accupressure points when applied to a limb, the neck, the waist, or the chest. The therapy pad 210 is similar to the pads 10 and 110 shown in FIGS. 3 and 4 with similar reference numerals referring to similar parts. According to this embodiment, a plurality of magnetic strips, e.g. 216*a*–216*i*, are arranged spaced apart from each other within the envelope 212. The locations of the magnetic strips may be maintained by spacers (not shown), by gluing or otherwise affixing the strips to the envelope 212, or by welding the envelope 212 along lines separating the strips 216*a*–216*i*. As mentioned above, the therapy pad 210 may be dimensioned to fit around a limb, the neck, the waist, or the chest. Moreover, the Dimensions of the VELCRO® pads 222, 224, 223, 225 may be chosen to provide the pad 210 with a wide degree of adjustability so that it may be affixed to different sized limbs, necks, waists, or the chests.

Figure 6:
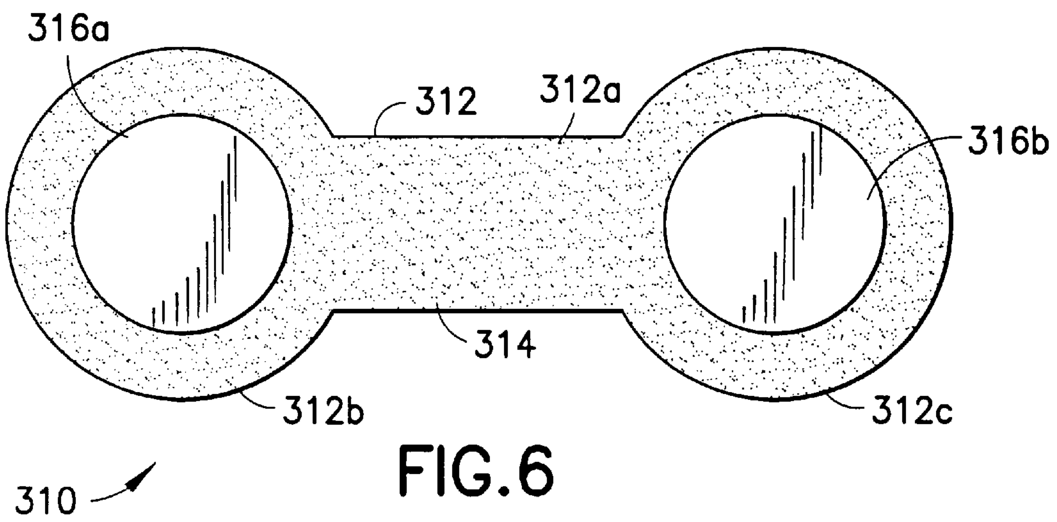
FIG. 6 is a transparent plan view of a cold therapy pad according to the invention shaped to be placed over the eyes.

Turning now to FIG. 6, a cold therapy pad 310 according to the invention is designed to be placed over the eyes. Accordingly, the envelope 312 has a narrow central portion 312*a* dimensioned to fit over the bridge of the nose and two larger circular end portions 312*b*, 312*c*. The entire envelope 312 is filled with freezing gel 314 and two circular magnets 316*a*, 316*b* are respectively located in the two circular end portions 312*b*, 312*c*. If desired, a third flexible magnet may be located in the narrow central portion 312*a* of the envelope 312. Alternatively, a single magnet having the same shape a, the envelope 312 may be provided. Still alternatively, magnets may be omitted from the circular end portions 312*b*, 312*c* and only provided in the narrow central portion 312*a*. It is likely not necessary to provide any fixation means such as VELCRO® since the pad 310 is likely to be used when the user is in a supine position.

Figure 7:
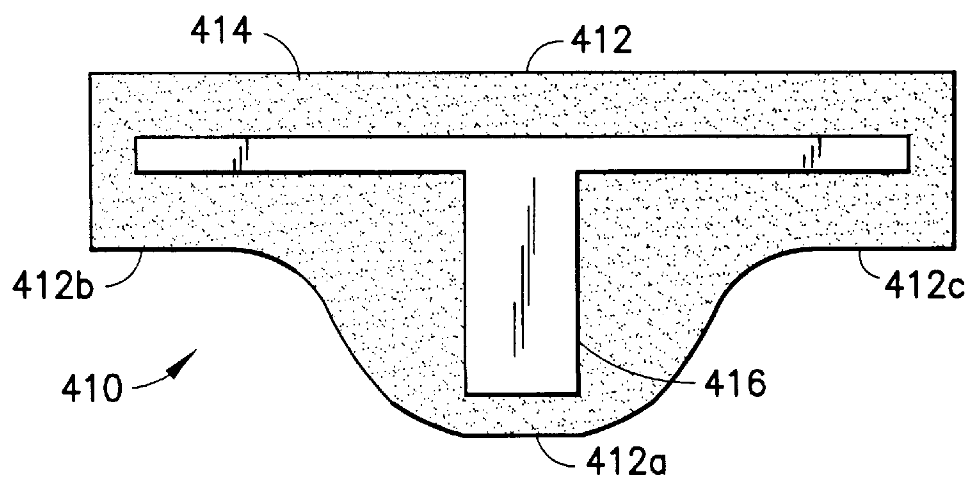
FIG. 7 is a transparent plan view of a cold therapy pad according to the invention shaped to be placed around the neck.

Still another embodiment of a cold therapy pad 410 is shown in FIG. 7. The cold pad 410 is designed to be worn around the neck. Accordingly, the envelope 412 has a broad central portion 412*a* and relatively narrow end portions 412*b*, 412*c*. As in the other embodiments, the envelope 412 is filled with a freezing gel 414 and a flexible magnet 416. In this embodiment, the magnet 416 is substantially T-shaped. When worn around the neck, the central broad portion 412*a* of the pad 410 is dimensioned to overlie either the nape of the neck or the upper sternum. When dimensioned large enough, the ends 412*b*, 412*c* will overlie the shoulders and no fixation means need be provided. Alternatively, VELCRO® pads may be provided at the ends 412*b*, 412*c* as described above with reference to FIGS. 3–5.

There have been described and illustrated herein several embodiments of a cold therapy pad with a magnetic insert. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials could be utilized if they provide substantially the same function in the same way to achieve the same result. Also, while several specifically shaped and sized embodiments have been shown, it will be recognized that other shapes and sizes might be used with similar results obtained. Moreover, while particular configurations have been disclosed in reference to a single flexible permanent magnet or multiple flexible magnets inside the envelope, it will be appreciated that other configurations could be used with multiple small non-flexible magnets spaced apart from each other inside the envelope. It will therefore be appreciated by those skilled in the art that yet other modifications could be made to the provided invention without deviating from its spirit and scope as so claimed.

What is claimed is:

1. A cold therapy pad, comprising:

a) a flexible envelope;

b) a high thermal capacity gel which changes from liquid to slush at a temperature well below human body temperature and which requires considerable heat energy when it warms through a change of state from slush to liquid said gel being contained within said flexible envelope; and c) at least one permanent magnet contained inside said flexible envelope.

2. A cold therapy pad according to claim 1, wherein:

said at least one permanent magnet is a flexible permanent magnet.

3. A cold therapy pad according to claim 1, wherein:

said at least one permanent magnet is a plurality of flexible permanent magnets.

4. A cold therapy pad according to claim 1, wherein: said at least one permanent magnet is substantially centrally located within said gel.

5. A cold therapy pad according to claim 1, wherein: said at least one permanent magnet is located substantially between said gel and said envelope.

6. A cold therapy pad according to claim 1, wherein: said envelope is made of a flexible polymer.

7. A cold therapy pad according to claim 1, wherein: said gel is made of silicate.

8. A cold therapy pad according to claim 1, wherein: said permanent magnet is made of molten metal hardened in an electric field.

9. A cold therapy pad according to claim 1, wherein: said envelope is substantially rectangular.

10. A cold therapy pad according to claim 1, wherein: said envelope is dimensioned to fit around a human joint and is provided with a central opening which overlies the joint when placed around the joint.

11. A cold therapy pad, comprising:

a) a flexible envelope;

b) a high thermal capacity gel which will remain cold for a period of time, said gel being contained within said flexible envelope; and c) at least one permanent magnet contained inside said flexible envelope, wherein said envelope is dimensioned to fit around a human joint and is provided with a central opening which overlies the joint when placed around the joint, and said at least one permanent magnet includes a substantially circular magnet having a central opening which is substantially coaxial with said central opening in said envelope.

12. A cold therapy pad according to claim 1, wherein: said envelope has a relatively narrow middle portion and two relatively broad end portions and said envelope is dimensioned for said broad end portions to fit over the eyes of a user.

13. A cold therapy pad according to claim 1, wherein: said envelope has a relatively broad middle portion and two relatively narrow end portions and said envelope is dimensioned for said narrow end portions to fit around the neck of a user with said relatively broad middle portion overlying either the nape or the upper sternum of the user.

14. A cold therapy pad according to claim 1, further comprising:

d) fixation means for attaching said flexible envelope to a body part of a user.

15. A cold therapy pad according to claim 14, wherein: said fixation means includes a pair of mating VELCRO® strips attached to opposite ends of said envelope.

16. A cold therapy pad, comprising:

a) a flexible envelope;

b) a high thermal capacity gel slush at a temperature well below human body temperature, said gel slush requiring considerable heat energy to change its state from slush to liquid, said gel slush being contained within said flexible envelope; and c) at least one permanent magnet contained inside said flexible envelope.

17. A cold therapy pad according to claim 16, wherein: said gel is made of silicate.

18. A cold therapy pad according to claim 16, wherein: said at least one permanent magnet comprises at least one flexible permanent magnet.

19. A cold therapy pad according to claim 16, wherein: said at least one permanent magnet is either substantially centrally located within said gel or is located substantially between said gel and said envelope.

20. A cold therapy pad according to claim 16, further comprising:

d) fixation means for attaching said flexible envelope to a body part of a user, wherein said envelope has either a relatively narrow middle portion and two relatively broad end portions and is dimensioned for said broad end portions to fit over the eyes of a user, or said envelope has a relatively broad middle portion and two relatively narrow end portions and is dimensioned for said narrow end portions to fit around the neck of a user with said relatively broad middle portion overlying either the nape or the upper sternum of the user.

* * * * *